(12) United States Patent
Komatsu et al.

(10) Patent No.: US 7,005,540 B2
(45) Date of Patent: Feb. 28, 2006

(54) METHOD OF PURIFYING AROMATIC POLYCARBOXYLIC ACID

(75) Inventors: Makoto Komatsu, Ibaraki (JP); Masato Inari, Okayama (JP)

(73) Assignee: Mitsubishi Gas Chemical Company, Inc., Tokyo (JP)

(*) Notice: Subject to any disclaimer, the term of this patent is extended or adjusted under 35 U.S.C. 154(b) by 0 days.

(21) Appl. No.: 10/476,148

(22) PCT Filed: Apr. 23, 2002

(86) PCT No.: PCT/JP02/04037

§ 371 (c)(1),
(2), (4) Date: Oct. 27, 2003

(87) PCT Pub. No.: WO02/088066

PCT Pub. Date: Nov. 7, 2002

(65) Prior Publication Data

US 2004/0133038 A1    Jul. 8, 2004

(30) Foreign Application Priority Data

Apr. 27, 2001  (JP) ............................. 2001-131093

(51) Int. Cl.
*C07C 51/42*   (2006.01)
(52) U.S. Cl. ................... 562/485; 562/486; 562/487
(58) Field of Classification Search ............... 562/485, 562/486, 487
See application file for complete search history.

(56) References Cited

U.S. PATENT DOCUMENTS 5,362,908 A * 11/1994 Schroeder et al. .......... 562/487

FOREIGN PATENT DOCUMENTS

| JP | 07-017903 | | 1/1995 |
| JP | 2000-001456 | * | 1/2000 |
| JP | 2001-096157 | | 4/2001 |
| WO | WO 94/20447 | | 9/1994 |

OTHER PUBLICATIONS

Aldrich Catalog Handbook of Fine Chemicals, p. 187, 1998-1999.*

* cited by examiner

*Primary Examiner*—Cecilia J. Tsang
*Assistant Examiner*—Taylor Victor Oh
(74) *Attorney, Agent, or Firm*—Antonelli, Terry, Stout and Kraus, LLP

(57) ABSTRACT

Crude polycarboxylic acid is slurried in an aqueous medium and the slurry is brought into contact with a metal catalyst while preventing catalyst components thereof from contaminating crystals. Since hydrogenation or decarbonylation of a polymerization inhibitory substance or a substance causing coloration can efficiently proceed at a low temperature while suppressing side reactions, a product having such a quality as to permit direct use thereof as such for polymerization can be obtained with good productivity. Also, since the contact temperature can be lowered, simplification of apparatus and energy saving may be attained.

14 Claims, No Drawings

METHOD OF PURIFYING AROMATIC POLYCARBOXYLIC ACID

TECHNICAL FIELD

The present invention relates to a method of purifying a crude aromatic polycarboxylic acid and, more specifically, to a purification method in which a crude aromatic polycarboxylic acid obtained by liquid phase oxidation of a polyalkyl aromatic hydrocarbon is purified by the removal of polymerization inhibitory substances and substances causing coloration therefrom to give a purified aromatic polycarboxylic acid which can be used directly as such for the polymerization resulting in a high molecular weight, colorless polyester resin, etc.

BACKGROUND ART

Aromatic polycarboxylic acids are commercially important substances as chemical intermediates. Thus, there is a wide demand for aromatic polycarboxylic acids as raw materials of polyesters, polyamides, polyimides, liquid crystal polymers, etc. which are used for fibers, bottles, films and electronic applications.

As currently widely industrially used aromatic polycarboxylic acids, there may be mentioned terephthalic acid, isophthalic acid, phthalic acid, trimellitic acid, pyromellitic acid, 2,6-naphthalenedicarboxylic acid, 4,4'-biphenyldicarboxylic acid, 1,4,5,8-naphthalenetetracarboxylic acid and 3,3',4,4'-biphenyltetracarboxylic acid.

Known methods for the preparation of an aromatic polycarboxylic acid include a method in which a polyalkyl aromatic hydrocarbon such as xylene, dialkylnaphthalene, dialkylbiphenyl, tetraalkylnaphthalene or tetraalkylbiphenyl is oxidized with molecular oxygen at a high temperature and a high pressure in the presence of a heavy metal such as Co or Mn and a bromine compound in an acetic acid solvent, and a method in which the polyalkyl aromatic hydrocarbon is oxidized with air in the presence of nitric acid, chromic acid or the like. The aromatic polycarboxylic acid obtained by the above oxidation reaction contains impurities such as monocarboxylic acids and aldehydes which are intermediate products of the oxidation reaction, bromine adducts and metal components which are derived from the catalyst and coloring substances having unknown structures.

As a recent increase of necessity for recycling plastic materials such as polyesters, materials are now recycled and reused through, for example, decomposition of PET bottles. In general, however, aromatic polycarboxylic acids obtained by the above decomposition contain impurities such as colored substances and foreign matters.

When the aromatic polycarboxylic acids containing such impurities are used as raw materials for the polymerization with diols or diamines, physical and mechanical properties, such as heat resistance, mechanical strengths and dimensional stability, of the obtained resins are inferior. Therefore, such aromatic polycarboxylic acids cannot be used as raw materials for polyesters, polyamides and polyimides. Further, crude aromatic polycarboxylic acids obtained by oxidation are generally colored yellow or black and cannot be used as such for applications requiring transparency such as bottles and films.

In this circumstance, as a method of purifying terephthalic acid, for example, a method is widely used in which a crude terephthalic acid is completely dissolved in water as a solvent at a high temperature of 260 to 280° C. The solution is then subjected to hydrogenation using a palladium catalyst supported on activated carbon so that impurities such as polymerization inhibitory substances and substances causing coloration are reduced. From the resulting solution, terephthalic acid is crystallized. By this method, purified terephthalic acid capable of being directly used as such for polymerization may be obtained (Japanese Patent Publication No. 41-16860).

The above method is for terephthalic acid which is easily soluble in water at a high temperature. In order to improve productivity, however, it is necessary to use a temperature as high as 260 to 280° C. and, accordingly, to use a high pressure. Because such a high temperature is used, side reactions such as hydrogenation on the nucleus are apt to occur and, further, it is necessary to select materials of the apparatus while taking corrosion thereof into consideration.

In the case of naphthalenedicarboxylic acid and biphenyldicarboxylic acid, since the solubility thereof in water is about 1/10 of that of terephthalic acid, it is necessary to use much higher temperature than 280° C. in order to conduct the above purification method with high productivity. This causes extreme difficulty in practical use.

Purification of an organic compound is generally performed by distillation, crystallization, adsorption or a combination of these operations. Since aromatic polycarboxylic acids have a self-decomposition temperature which is lower than the boiling point thereof, the purification by distillation is substantially impossible. Further, since aromatic polycarboxylic acids have poor solubility in commonly industrially used solvents, the purification by crystallization involves difficulties. In particular, since naphthalenepolycarboxylic acid and biphenylpolycarboxylic acid are hardly soluble in various solvents, industrially advantageous processes for producing high purity naphthalenepolycarboxylic acid or high purity biphenylpolycarboxylic acid have not yet been established.

DISCLOSURE OF THE INVENTION

It is an object of the present invention to provide a method of purifying an aromatic polycarboxylic acid capable of efficiently purifying aromatic polycarboxylic acid, which is difficult to be purified as described above, to give the aromatic polycarboxylic acid which can be used directly as such for the polymerization resulting in a high molecular weight, colorless polyester resin, etc.

The inventors have made an earnest study on a method of purifying an aromatic polycarboxylic acid which method has such problems as described above. As a result, it has been found that when the aromatic polycarboxylic acid is contacted with a metal catalyst in the absence of oxygen, while maintaining the aromatic polycarboxylic acid in a slurried state, i.e. at such a temperature that the aromatic polycarboxylic acid dissolved in an aqueous medium exists together with undissolved aromatic polycarboxylic acid, and while preventing catalytic components from contaminating the purified aromatic polycarboxylic acid, impurities such as intermediate products of the oxidation reaction and coloring substances can be removed by hydrogenation or decarbonylation at a low temperature while preventing the production of by-products so that the purification can be achieved with a good productivity to give aromatic polycarboxylic acid which can be used directly as such for the polymerization resulting in a high molecular weight, colorless polyester resin, etc. The present invention has been made on the basis of the above finding.

Thus, the present invention provides a method of purifying an aromatic polycarboxylic acid, comprising a step of slurrying a crude aromatic polycarboxylic acid in an aqueous medium and a step of bringing the slurry into contact with a metal catalyst in the absence of oxygen while preventing catalyst components from contaminating crystals.

BEST MODE FOR CARRYING OUT THE INVENTION

The aromatic polycarboxylic acid used for the purpose of the present invention is an aromatic hydrocarbon, such as benzene, naphthalene or biphenyl, to which two or more carboxyl groups are linked. A method of producing such an aromatic polycarboxylic acid is not specifically limited. For example, the aromatic polycarboxylic acid may be obtained by oxidizing a raw material compound obtained by introducing an alkyl group such as a methyl group, an ethyl group or an isopropyl group and a plurality of functional groups capable of forming carboxyl groups by oxidation, such as formyl groups and acetyl groups, into the above-mentioned aromatic hydrocarbon.

As aromatic polycarboxylic acids which are currently industrially widely used, there may be mentioned terephthalic acid, isophthalic acid, phthalic acid, trimellitic acid, pyromellitic acid, 2,6-naphthalenedicarboxylic acid, 4,4'-biphenyldicarboxylic acid, 1,4,5,8-naphthalenetetracarboxylic acid and 3,3',4,4'-biphenyltetracarboxylic acid.

Formylated compounds produced as intermediate compounds during the course of the production of aromatic polycarboxylic acid by oxidation of an aromatic hydrocarbon having a plurality of substituents, such as 4-carboxybenzaldehyde in the case of the production of terephthalic acid and formylnaphthoic acid in the case of the production of naphthalenedicarboxylic acid, are impurities which are difficult to be removed and which act as polymerization inhibitory substances and substances causing coloration in the subsequent polymerization stage.

In the method of the present invention, the above-describe polymerization inhibitory substances and substances causing coloration contained in a crude aromatic polycarboxylic acid are hydrogenated or decarbonylated by contact with a metal catalyst in the absence of oxygen. When the contact with the metal catalyst is carried out in the presence of hydrogen, the polymerization inhibitory substances and substances causing coloration are hydrogenated. When the contact with the metal catalyst is carried out in the absence of hydrogen and oxygen, the polymerization inhibitory substances and substances causing coloration are decarbonylated. By this way, the impurities are removed.

Any metal catalyst may be used as the hydrogenation or decarbonylation catalyst as long as it has an activity and is hardly deactivated in the purification conditions. A catalyst having a carrier on which catalytic components are supported is generally used.

As metals to be supported, there may be mentioned Group 8 metals, namely noble metals such as platinum, palladium, ruthenium, rhodium, osmium and iridium, cobalt and nickel. As the carrier, activated carbon is preferably used for reasons of resistance to aromatic carboxylic acid-containing high temperature aqueous solution.

The temperature and pressure at which the hydrogenation or decarbonylation is performed vary with the kind of the aromatic polycarboxylic acid to be purified, the conditions of the impurities and the catalyst used and are selected so that the hydrogenation or decarbonylation of the polymerization inhibitory substances and substances causing coloration can be efficiently achieved while preventing occurrence of side reactions.

The present invention is characterized in that the aromatic polycarboxylic acid is contacted with a metal catalyst while maintaining the aromatic polycarboxylic acid in a slurried state, i.e. at such a state that a portion of the aromatic polycarboxylic acid is dissolved in an aqueous medium, and while preventing catalytic components from contaminating the purified aromatic polycarboxylic acid.

Thus, at the outset, the temperature at which the hydrogenation or decarbonylation is carried out is so selected that the dissolved aromatic polycarboxylic acid and undissolved aromatic polycarboxylic acid coexist in the form of a slurry, though the temperature varies with the kind of the aromatic polycarboxylic acid to be purified.

For example, since the solubility of terephthalic acid in water at 230° C. is 6.5 g/100 g, a slurry in which dissolved terephthalic acid and undissolved terephthalic acid coexist is formed when the amount of terephthalic acid relative to water is beyond the solubility.

Since the hydrogenation or decarbonylation is carried out for a slurry containing undissolved aromatic polycarboxylic acid rather than for a homogeneous aqueous solution, it is necessary to contrive a way for using the catalyst.

Namely, it is necessary to retain the metal catalyst so that the catalyst and the undissolved aromatic polycarboxylic acid are prevented from being mixed together. For example, the catalyst particles can be prevented from being mixed into the purified aromatic polycarboxylic acid by holding the catalyst in a basket through which only the slurry is permitted to pass and by immersing the basket in the slurry.

The concentration of the slurry is so selected that the hydrogenation or decarbonylation of the purities is not hindered and that the slurry can be transferred using an ordinary industrial means.

When the aromatic polycarboxylic acid is contacted with the metal catalyst in the presence of hydrogen, the hydrogenation can be achieved by injecting hydrogen into water as a solvent in which part of the aromatic polycarboxylic acid is dissolved.

The hydrogen partial pressure in the hydrogenation is so selected that the hydrogenation of the aromatic nucleus of the aromatic polycarboxylic acid is prevented from occurring at the selected temperature as described above but that the hydrogenation of the formylated compounds acting as polymerization inhibitory substances and substances causing coloration can efficiently proceed.

Namely, when hydrogenation proceeds excessively, impurities will increase. Thus, the hydrogen partial pressure in the hydrogenation is preferably 0.1 to 3 MPa.

When the aromatic polycarboxylic acid is contacted with the metal catalyst in the absence of hydrogen and oxygen, it is necessary to substitute the atmosphere in the system with an inert gas such as nitrogen so that oxygen is completely removed.

In the present invention, the term "in the absence of oxygen" is intended to refer to the state in which the atmosphere in the system is substituted with an inert gas such as nitrogen so that oxygen completely disappears in the system, i.e. in which the oxygen content is 1 ppm or less, preferably 0.1 ppm or less. As the inert gas to be used for this purpose is most generally nitrogen. Argon may be used. Carbon dioxide is not preferable.

The residence time varies with the kind of the aromatic polycarboxylic acid to be purified and the state of the impurities but is so selected that the hydrogenation or decarbonylation can be nearly completed. In general, the residence time is 0.5 to 5 h.

Generally, when the hydrogenation or decarbonylation is nearly completed, the mixture is cooled to near room temperature. The crystals thus obtained are rinsed with warm water, etc. and then dried to obtain a purified aromatic polycarboxylic acid.

According to the present invention, since a large amount of water required to completely dissolve the aromatic polycarboxylic acid is not used, the volume of the reactor used can be small and the purification of the aromatic polycarboxylic acid can be carried out efficiently.

Also, according to the present invention, it is not necessary to heat to a temperature required to completely dissolve the aromatic polycarboxylic acid. Therefore, devices and utility for heating to a high temperature are not needed. Further, it is possible to avoid excessive hydrogenation or decarbonylation, the elimination by decomposition of carboxyl groups and the formation of polymerization inhibitory substances and substances causing coloration which would be otherwise caused by heating to a high temperature. Hence, high purity aromatic polycarboxylic acid can be easily obtained.

Additionally, according to the present invention, it is possible to purify an aromatic polycarboxylic acid which is substantially impossible to be purified by distillation because the self-decomposition temperature thereof is lower than the boiling point thereof and which is difficult to be purified by crystallization because the solubility thereof in a solvent is low. Further, it is possible to obtain an aromatic polycarboxylic acid which can be used directly as such for the polymerization to give a high molecular weight, colorless polyester resin, etc.

EXAMPLES

The present invention will be described more concretely by way of examples and comparative examples. The present invention is, however, not limited to the examples.

In the present invention, $OD_{340}$ and $OD_{400}$ which are factors showing the degree of containing coloring impurities are measured values obtained as follows:

$OD_{340}$: 2 g of terephthalic acid are dissolved in 25 ml of 2N KOH and the solution is charged in a 50 mm cell. Absorbance at 340 nm is measured.

$OD_{400}$: 1 g of naphthalenedicarboxylic acid is dissolved in 10 ml of 1N KOH and the solution is charged in a 10 mm cell. Absorbance at 400 nm is measured.

The values reflect the amount of coloring impurities and substances causing coloration contained in terephthalic acid and naphthalenedicarboxylic acid. The lower the value, the smaller is the amount of the coloring impurities.

Example 1

A crude terephthalic acid (150 g) containing 3,500 ppm of 4-carboxybenzaldehyde (hereinafter referred to as 4CBA) and showing $OD_{340}$ of 1.0 and 600 g of water were charged in an autoclave equipped with a stirrer. To the stirrer, two baskets each provided with holes for passage of a terephthalic acid slurry were attached. In the baskets, 20 g of coconut hull activated carbon supporting 0.5% of Pd were contained. After closing the autoclave, a hydrogen partial pressure of 0.2 MPa was established therein. With stirring, the contents in the autoclave were heated to 230° C. From the solubility of terephthalic acid in water at 230° C., the amount of terephthalic acid dissolved in 600 g of water is calculated as 39 g. Heating was stopped 2 h after the temperature of 230° C. had been reached. After cooling to room temperature, terephthalic acid was recovered, rinsed with water at 90° C. and dried. The terephthalic acid thus obtained was found to contain 10 ppm of 4CBA and to show $OD_{340}$ of 0.1.

The terephthalic acid was polycondensed with ethylene glycol to obtain a polyester. Pellets of the thus formed polyester were transparent.

Example 2

A crude 2,6-naphthalenedicarboxylic acid (150 g) containing 2,600 ppm of formylnaphthoic acid and showing $OD_{400}$ of 1.0 and 600 g of water were charged in an autoclave, similar to that used in Example 1, equipped with a stirrer. To the stirrer, two baskets containing 20 g of the same catalyst as used in Example 1 were attached. After hydrogen partial pressure of 0.2 MPa had been established, the temperature was increased to 280° C. with stirring. From the solubility of 2,6-naphthalenedicarboxylic acid in water at 280° C., the amount of 2,6-naphthalenedicarboxylic acid dissolved in 600 g of water is calculated as 36 g. Heating was stopped 2 h after the temperature of 280° C. had been reached. After cooling to room temperature, 2,6-naphthalenedicarboxylic acid was recovered, rinsed with water at 90° C. and dried. The 2,6-naphthalenedicarboxylic acid thus obtained was found to contain 10 ppm of formylnaphthoic acid and to show $OD_{400}$ of 0.040.

The 2,6-naphthalenedicarboxylic acid was polycondensed with ethylene glycol to obtain a polyester. Pellets of the thus formed polyester were transparent.

Example 3

A crude terephthalic acid (150 g) containing 3,500 ppm of 4CBA and showing $OD_{340}$ of 1.5 and 600 g of water were charged in an autoclave equipped with a stirrer. To the stirrer, two baskets each provided with holes for passage of a terephthalic acid slurry were attached. In the baskets, 20 g of coconut hull activated carbon supporting 0.5% by weight of Pd were contained. After closing the autoclave, nitrogen was fed so that the pressure therein was increased to 2 MPa. Then the pressure was released to atmospheric pressure. Such procedures were repeated five times so that oxygen contained in the system was completely substituted. Then, with stirring, the contents in the autoclave were heated to 230° C. From the solubility of terephthalic acid in water at 230° C., the amount of terephthalic acid dissolved in 600 g of water is calculated as 39 g. Heating was stopped 2 h after the temperature of 230° C. had been reached. After cooling to room temperature, terephthalic acid was recovered, rinsed with water at 90° C. and dried.

The terephthalic acid thus obtained was found to contain 10 ppm of 4CBA and to show $OD_{340}$ of 0.16. The terephthalic acid was polycondensed with ethylene glycol to obtain a polyester. Pellets of the thus formed polyester were transparent.

Comparative Example 1

The procedures of Example 3 were repeated in the same manner as described using the same apparatus and raw materials as those in Example 3, except that oxygen in the system after charging of the raw materials was not substituted with nitrogen. As a result, the product was found to contain 11 ppm of 4CBA and to show $OD_{340}$ of 0.34. The terephthalic acid was polycondensed with ethylene glycol to obtain a polyester. Pellets of the thus formed polyester were slightly colored.

Example 4

A crude 2,6-naphthalenedicarboxylic acid (80 g) containing 1,400 ppm of formylnaphthoic acid and showing $OD_{400}$ of 1.0 and 600 g of water were charged in an autoclave, similar to that used in Example 3, equipped with a stirrer. To the stirrer, two baskets containing 20 g of coconut hull activated carbon supporting 0.5% by weight of Pd were attached in the same manner as in Example 3. After closing the autoclave, nitrogen was fed so that the pressure therein was increased to 2 MPa. Then the pressure was released to atmospheric pressure. Such procedures were repeated five times so that oxygen contained in the system was completely substituted. Thereafter, with stirring, the contents in the autoclave were heated to 280° C. From the solubility of 2,6-naphthalenedicarboxylic acid in water at 280° C., the amount of 2,6-naphthalenedicarboxylic acid dissolved in 600 g of water is calculated as 36 g. Heating was stopped 2 h after the temperature of 280° C. had been reached. After cooling to room temperature, 2,6-naphthalenedicarboxylic acid was recovered, rinsed with water at 90° C. and dried. The 2,6-naphthalenedicarboxylic acid thus obtained was found to contain 50 ppm of formylnaphthoic acid and to show $OD_{400}$ of 0.10. The 2,6-naphthalenedicarboxylic acid was polycondensed with ethylene glycol to obtain a polyester. Pellets of the thus formed polyester were transparent.

Comparative Example 2

The procedures of Example 4 were repeated in the same manner as described using the same raw materials as those in Example 4, except that the catalyst-containing baskets were not attached. As a result, the product was found to contain 1,350 ppm of 4CBA and to show $OD_{340}$ of 0.9. The terephthalic acid was polycondensed with ethylene glycol to obtain a polyester. Pellets of the thus formed polyester were colored.

Example 5

The same crude 2,6-naphthalenedicarboxylic acid (150 g) as used in Example 4 and 600 g of water were charged in an autoclave, similar to that used in Example 3, equipped with a stirrer. To the stirrer, two baskets containing 20 g of coconut hull activated carbon supporting 0.5% by weight of Pd were attached in the same manner as in Example 3. After closing the autoclave, hydrogen was fed so that the pressure therein was increased to 2 MPa. Then the pressure was released to atmospheric pressure. Such procedures were repeated five times so that oxygen contained in the system was completely substituted. After hydrogen partial pressure of 0.2 MPa had been established, the temperature was increased to 280° C. with stirring. From the solubility of 2,6-naphthalenedicarboxylic acid in water at 280° C., the amount of 2,6-naphthalenedicarboxylic acid dissolved in 600 g of water is calculated as 36 g. Heating was stopped 2 h after the temperature of 280° C. had been reached. After cooling to room temperature, 2,6-naphthalenedicarboxylic acid was recovered, rinsed with water at 90° C. and dried. The 2,6-naphthalenedicarboxylic acid thus obtained was found to have a formylnaphthoic acid content below the detectable limit and to show $OD_{340}$ of 0.06. The 2,6-naphthalenedicarboxylic acid was polycondensed with ethylene glycol to obtain a polyester. Pellets of the thus formed polyester were transparent.

INDUSTRIAL APPLICABILITY

According to the present invention, by converting a crude aromatic polycarboxylic acid into a slurry in an aqueous medium and by bringing the slurry into contact with a metal catalyst in the absence of oxygen to carry out the hydrogenation or decarbonylation of the polymerization inhibitory substances and substances causing coloration while preventing catalyst components from contaminating crystals, the temperature of the purification operation can be lowered. Therefore, side reactions can be suppressed and a product having such a quality as to permit direct use thereof as such for polymerization can be obtained with good productivity. Also, simplification of apparatus and energy saving may be attained.

Accordingly, in accordance with the method of the present invention, aromatic polycarboxylic acids which have been hitherto difficult to be purified can be now purified with good efficiency in an extremely industrially advantageous manner.

What is claimed is:

1. A method of purifying aromatic polycarboxylic acid, comprising a step of slurrying a crude aromatic polycarboxylic acid in an aqueous medium and a step of bringing the slurry into contact with a Group 8 metal catalyst in the absence of oxygen while maintaining the aromatic polycarboxylic acid in a slurried state at such a temperature that aromatic polycarboxylic acid dissolved in the aqueous medium exists together with undissolved aromatic polycarboxylic acid and while preventing the catalyst from contaminating crystals, wherein said contact with the Group 8 metal catalyst is performed in the absence of oxygen and hydrogen.

2. The method according to claim 1, wherein the metal catalyst comprises a carrier and the Group 8 metal supported on the carrier.

3. The method according to claim 1, wherein a basket in which the Group 8 metal catalyst is held is immersed into the slurry, so that the catalyst is prevented from contaminating the crystals of the purified aromatic polycarboxylic acid.

4. The method according to claim 1, wherein the aromatic polycarboxylic acid is terephthalic acid.

5. The method according to claim 1, wherein the aromatic polycarboxylic acid is 2,6-naphthalenedicarboxylic acid.

6. The method according to claim 1, wherein the aromatic polycarboxylic acid is 4,4-biphenyldicarboxylic acid.

7. The method according to claim 2, wherein a basket in which the Group 8 metal catalyst is held is immersed into the slurry so that the catalyst is prevented from contaminating the crystals of the purified aromatic polycarboxylic acid.

8. A method of purifying aromatic carboxylic acid, comprising a step of slurrying a crude aromatic polycarboxylic acid in an aqueous medium and a step of bringing the slurry into contact with a Group 8 metal catalyst in the absence of oxygen and hydrogen while preventing catalyst from contaminating crystals.

9. The method according to claim 8, wherein the metal catalyst comprises a carrier and the Group 8 metal supported on the carrier.

10. The method according claim 9, wherein a basket in which the Group 8 metal catalyst is held is immersed into the slurry, so that the catalyst is prevented from contaminating the crystals of the purified aromatic polycarboxylic acid.

11. The method according to claim 8, wherein a basket in which the Group 8 metal catalyst is held is immersed into the slurry, so that the catalyst is prevented from contaminating the crystals of the purified aromatic polycarboxylic acid.

12. The method according to claim 8, wherein the aromatic polycarboxylic acid is terephthalic acid.

13. The method according to claim 8, wherein the aromatic polycarboxylic acid is 2,6-naphthalenedicarboxylic acid.

14. The method according to claim 8, wherein the aromatic polycarboxylic acid is 4,4-biphenyldicarboxylic acid.

* * * * *